United States Patent [19]

Maillefer et al.

[11] Patent Number: 5,676,541
[45] Date of Patent: Oct. 14, 1997

[54] SET OF INSTRUMENTS OF INCREASING DIMENSION FOR THE BORING OF RADICULAR DENTAL CANALS

[75] Inventors: Michel Maillefer; Pierre-Luc Maillefer, both of Ballaigues, Switzerland

[73] Assignee: Maillefer Instruments S.A., Switzerland

[21] Appl. No.: 557,630

[22] Filed: Nov. 14, 1995

[51] Int. Cl.⁶ .................................................. A61C 5/02
[52] U.S. Cl. ............................................................. 433/102
[58] Field of Search ................................... 433/102, 224

[56] References Cited

U.S. PATENT DOCUMENTS

| | | | |
|---|---|---|---|
| 4,836,780 | 6/1989 | Buchanan | 433/102 |
| 4,971,556 | 11/1990 | Ritano | 433/102 |
| 5,017,138 | 5/1991 | Schilder | 433/102 |
| 5,026,284 | 6/1991 | Martin | 433/102 |
| 5,219,284 | 6/1993 | Velvart et al. | 433/102 |
| 5,380,200 | 1/1995 | Heath et al. | 433/102 |
| 5,503,554 | 4/1996 | Schoeffel | 433/102 |

*Primary Examiner*—Nicholas D. Lucchesi
*Attorney, Agent, or Firm*—Silverman, Cass & Singer, Ltd.

[57] ABSTRACT

A set of instruments for boring of radicular dental canals, in which the diameter D1 of each instrument, measured at the root of the pointed end portion thereof, varies according to a geometrical progression as well as the diameter D2 of each instrument measured at the root of the cutting edges. Hence, the variation is more pronounced for the diameters D2, larger than the diameters D1, than it is for the diameters D1. The conicity of the stem of the instruments increases in this manner from one instrument to another, so as to permit a the dentist to form the radicular canals with a specially funnelled shape which is best suited for some obturations, especially those to be treated with gutta-percha.

7 Claims, 1 Drawing Sheet

SET OF INSTRUMENTS OF INCREASING DIMENSION FOR THE BORING OF RADICULAR DENTAL CANALS

BACKGROUND OF THE INVENTION a) Field of the Invention

This invention relates to a set of instruments of increasing dimension for the boring of radicular dental canals in which each instrument comprises a conical stem presenting at least one helicoidal cutting edge.

b) Description of the Prior Art

Such sets of instruments, constituted by files and reamers, are known per se.

The instruments are formed with a series of terminal diameters, called D1, measured at the root of their ending portion which is not provided with a cutting edge. The diameter D1 of each instrument in the set is different, an is of a dimension, in most of the cases, of a value between 0.06 mm and 1.4 mm. The variation of the diameters D1 can be an arithmetical series, that is to say a linear series, or a geometric one. In these instruments, the conicity of the stem is constant, whatever the terminal diameter may be, this conicity being generally expressed not by its angle at the apex but by the difference between the terminal diameter D1 and the terminal diameter, called D2, measured at the root of the helicoidal cutting edge or edges. The lenght of the part of the stem presenting the said edge or edges being generally of 16 mm, the difference between the terminal diameter and the diameter of the stem at the root of the edge or edges is most generally of 0.32 mm.

The dentist who effects the boring of a radicular dental canal uses the instruments of the set while starting with an instrument of small diameter and while using then, successively, instruments of increasing diameter until the whole infected pulp is eliminated and the bored canal has a shape suitable for its obturation by means of gutta-percha or cement.

The most modern odontological technique requires that one gives to the radicular canal a funnelled shape, the canal being large at its cervical part, near the crown of the tooth, and having to remain very narrow at its apical part, in the vicinity of the end of the dental root. As a matter of fact, this funnelled shape of the radicular canals once they have been bored is more suitable for an obturation by means of gutta-percha, that is a technique which is more and more in use.

SUMMARY OF THE INVENTION

The object of the present invention is to permit to realize, more easily than with the usual conventional instruments, a funnelled shape of the radicular canals.

This object is achieved owing to the fact that the diameter D1 of each instrument, measured at the root of its terminal part, varies, from one instrument to another one, according to a geometrical progression, and by the fact that the diameter D2 of each instrument, measured at the root of its cutting part, varies too, from one instrument to another one, according to a geometrical progression.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilizing the same or equivalent principles may be used and structural changes may be made as desired by those skilled in the art without departing from the present invention and the purview of the appended claims.

DESCRIPTION OF THE PREFERRED EMBODIMENTS

Figure 1:
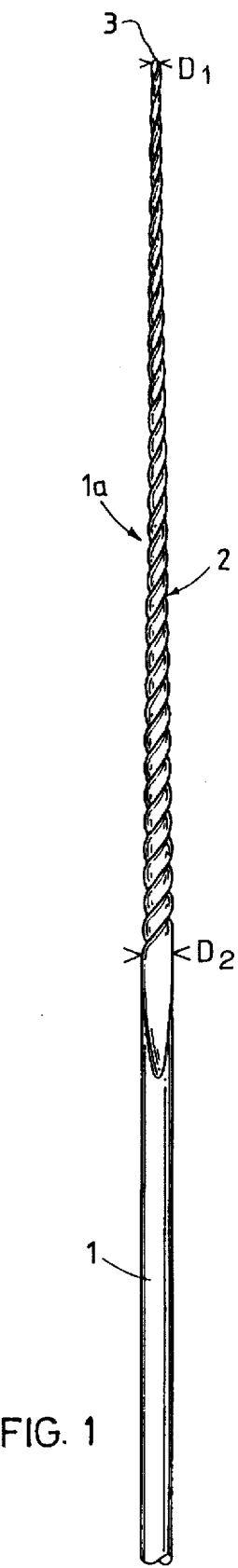
FIGS. 1, 2 and 3 are elevational views of three instruments for the boring of radicular dental canals belonging to a same set.
Figure 2:
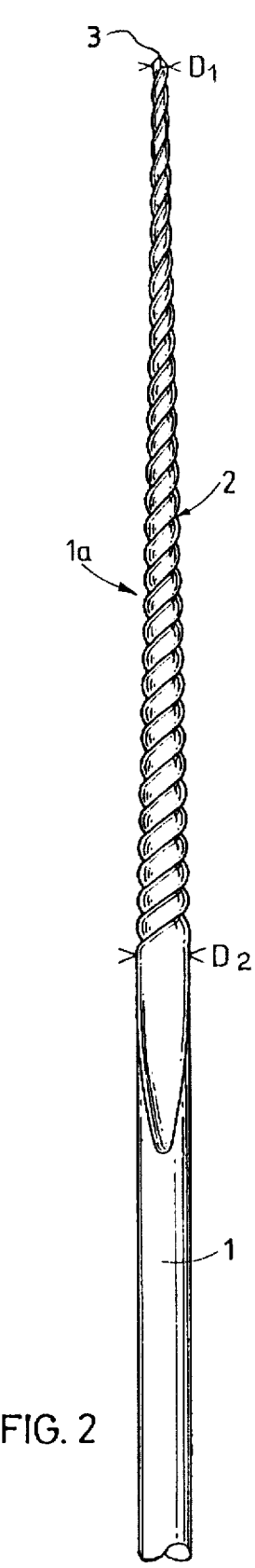
Figure 3:
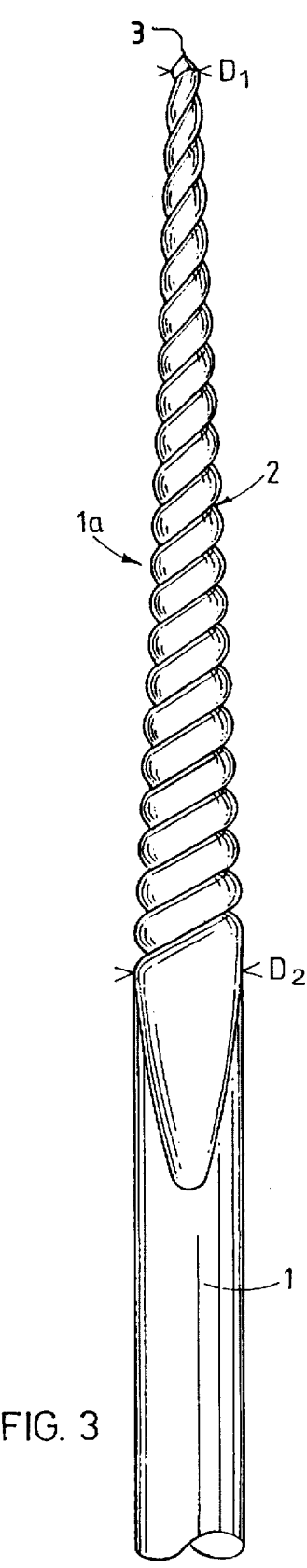

The instruments as represented, in the number of three, while a set of instruments can comprise up to about twenty, comprise each a cylindrical stem 1 intended to be engaged either into a handle permitting the manual operation of the instrument, or into a handle engaged in a handpiece producing the mechanical driving of the instrument.

The stem 1 is prolongated by a tapered portion 1a in which are provided helicoidal cutting edges 2 and which terminates at a conical point 3 which has no cutting edges.

One will obtain this instrument for instance while starting from a circular stem the front part 1a of which will be tapered by working, and while working therein plane faces so that the tapered portion has a polygonal section, for instance of triangular or square shape. One will then submit this stem to a torsion, thus realizing the helicoidal edges 2. One could also work the cutting edges directly on the stem at the moment of giving it its tapered shape.

The diameter of the stem at the root of its point, designated by D1, constitutes the nominal diameter serving to characterize the instrument, while the diameter designated by D2 is the diameter of the stem at the root of the cutting edges 2.

The several instruments of the set distinguish from each other by their dimension, the diameters D1 and D2 varying, from one instrument to another one, according to a geometrical progression.

The ratio of the geometrical progression of the diameters D1 could be the same as the ratio of the progression of the diameters D2. Since the diameters D2 are larger than the diameters D1, it follows that they increase more rapidly, so that the opening of the cone constituting the active part of the instruments increases, thereby imparting to the radicular canals a funnelled shape, in accordance with the object of the invention.

One could also provide that the ratio of the geometrical progression of the diameters D1 be higher than the ratio of the geometrical progression of the diameters D2 while providing that the D2 diameters continue to increase more than the diameters D1, and also providing that the opening of the cone constituting the active portion of the instruments does not increase too greatly.

One could also provide, for some applications, that the ratio of the geometrical progression of the diameters D1 be lower than the ratio of the geometrical progression of the diameters D2.

In this last case, however, the relatively high progression of the diameters D2 could have for a consequence that the instruments of large dimension (those which are situated at the end of the set) become too rigid with respect to the ones of small dimension. As a matter of fact, the increase of the diameter has obligatorily for consequence to increase the rigidity of the stems, that, if it is too strong, can constitute a drawback.

So that the flexibility of the different instruments of the set remains substantially the same, one could use different materials for the realization of the different instruments of the set or, at least, of some of them. One could also apply different thermic treatments to each instrument of the set or to a part thereof. One could also proceed to a different working of each instrument or of a part thereof, specially when the cutting edges are not obtained by a mere torsion of a tapered stem of polygonal section, so that the central part of the instruments remains substantially the same from one instrument to another one or does vary only according to a progression which is lower than that of the outer diameter of the instruments, so that the characteristics of flexibility be substantially maintained from one instrument to another one.

The ratio of the geometrical progression of the diameters D1 and D2 of the instruments of the set can be, for instance, of 20%. In this case, if the smallest instrument of the set has a diameter D1 of 0.06 mm and a diameter D2 of 0.092 mm, the diameters D1 and D2 of the second instrument will be of 0.072 mm and of 0.110 mm, respectively.

The following table indicates the diameters D1 and D2 of the eighteen instruments of the set in the specific case which is hereabove indicated, as well as, in the last column, the differences between D1 and D2. One sees that the difference is increasing, so that the opening of the cone of the tapered part of the instrument increases also.

Owing to this arrangement, the radicular canals which are bored by means of these instruments, used successively in the increasing order, will be more funnelled that the ones realized by means of conventional sets of instruments, that facilitates the obturations, especially by means of gutta-percha.

TABLE

| No  | Ø D1  | Ø D2  | D1–D2 |
|-----|-------|-------|-------|
| 6   | 0.06  | 0.092 | 0.032 |
| 7   | 0.072 | 0.110 | 0.038 |
| 8   | 0.086 | 0.132 | 0.046 |
| 1.0 | 0.103 | 0.159 | 0.056 |
| 1.2 | 0.124 | 0.191 | 0.067 |
| 1.4 | 0.149 | 0.229 | 0.080 |
| 1.7 | 0.179 | 0.274 | 0.095 |
| 2.1 | 0.215 | 0.330 | 0.115 |
| 2.5 | 0.258 | 0.396 | 0.138 |
| 3.1 | 0.310 | 0.475 | 0.165 |
| 3.7 | 0.372 | 0.570 | 0.198 |
| 4.4 | 0.446 | 0.683 | 0.237 |
| 5.3 | 0.535 | 0.820 | 0.285 |
| 6.4 | 0.642 | 0.984 | 0.342 |
| 7.7 | 0.770 | 1.181 | 0.411 |

TABLE-continued

| No   | Ø D1  | Ø D2  | D1–D2 |
|------|-------|-------|-------|
| 9.2  | 0.924 | 1.417 | 0.493 |
| 10.0 | 1.109 | 1.701 | 0.592 |
| 13.3 | 1.331 | 2.041 | 0.710 |

We claim:

1. A set of instruments for boring radicular dental canals, each instrument being of a diameter different than that of the other and comprising, a conical stem having a helicoidal cutting edge, the stem having an ending part with a diameter D1 measured at the root of said ending part, the cutting edge having a diameter D2 measured at the root of said cutting edge, the diameter D1 of each instrument varying from one instrument to another of the set according to a geometrical progression, and the diameter D2 of each instrument also varying from one instrument to another of the set according to a geometrical progression.

2. A set of instruments as claimed in claim 1 in which the geometrical progression according to which the diameters D1 vary has the same ratio as the geometrical progression according to which the diameters D2 vary.

3. A set of instruments as claimed in claim 1 in which the geometrical progression according to which the diameters D1 vary has a higher ratio than the geometrical progression according to which the diameters D2 vary.

4. A set of instruments as claimed in claim 1 in which the geometrical progression according to which the diameters D1 vary has a lower ratio than the geometrical progression according to which the diameters D2 vary.

5. A set of instruments as claimed in claim 1 in which at least part of the instruments of the set is formed of different material such that the flexibility of all of the instruments of the set is substantially the same notwithstanding the variations of the diameters of the several instruments of the set.

6. A set of instruments as claimed in claim 1 in which at least a part of the instruments of the set is submitted to different thermical treatments such that the flexibility of all of the instruments of the set is substantially the same notwithstanding the variations of the diameters of the several instruments of the set.

7. A set of instruments as claimed in claim 1 in which the cutting edge of at least a part of the instruments of the set is formed in different ways so that the diameter of the central part of the instruments does not vary substantially from one instrument to another, and thereby the flexibility of all of the instruments of the set is substantially the same.

* * * * *

UNITED STATES PATENT AND TRADEMARK OFFICE
CERTIFICATE OF CORRECTION

PATENT NO. : 5,676,541
DATED : October 14, 1997
INVENTOR(S) : Michel Maillefer and Pierre-Luc Maillefer It is certified that error appears in the above-indentified patent and that said Letters Patent is hereby corrected as shown below:

Abstract, line 9, delete "the";

Column 4, line 12, change "other" to --others--.

Signed and Sealed this

Ninth Day of December, 1997

Attest:

BRUCE LEHMAN

Attesting Officer

Commissioner of Patents and Trademarks